(12) United States Patent
　　　Scharf

(10) Patent No.: US 12,194,116 B2
(45) Date of Patent: Jan. 14, 2025

(54) COMPRESSED BODY EXFOLIATING DEVICE

(71) Applicant: Dave Scharf, Warren, OR (US)

(72) Inventor: Dave Scharf, Warren, OR (US)

( * ) Notice: Subject to any disclaimer, the term of this patent is extended or adjusted under 35 U.S.C. 154(b) by 301 days.

(21) Appl. No.: 17/867,847

(22) Filed: Jul. 19, 2022

(65) Prior Publication Data

US 2024/0024208 A1　　Jan. 25, 2024

(51) Int. Cl.
| | |
|---|---|
| *A61K 8/02* | (2006.01) |
| *A46B 9/00* | (2006.01) |
| *A47K 7/02* | (2006.01) |
| *A61Q 19/10* | (2006.01) |

(52) U.S. Cl.
　　CPC ............ *A61K 8/0208* (2013.01); *A47K 7/028* (2013.01); *A61Q 19/10* (2013.01); *A46B 9/005* (2013.01)

(58) Field of Classification Search
　　CPC ............ A47K 7/00; A47K 7/02; A47K 7/022; A47K 7/026; A47K 7/024; A47K 7/028
　　See application file for complete search history.

(56) References Cited

U.S. PATENT DOCUMENTS

| | | | |
|---|---|---|---|
| 3,146,479 A * | 9/1964 | Stoker | ..................... A47L 13/16 15/118 |
| 6,161,246 A | 12/2000 | Trachtenberg | |
| 7,255,704 B2 | 8/2007 | Hogan | |
| D613,906 S | 4/2010 | Moyer | |
| 8,141,196 B2 * | 3/2012 | Chen | ........................ A47K 7/02 15/209.1 |
| 8,967,898 B1 | 3/2015 | Dayeh | |
| 2006/0010625 A1 | 1/2006 | Tapper | |
| 2009/0304434 A1 * | 12/2009 | Girvan | ..................... A47K 7/02 401/188 R |
| 2010/0034573 A1 | 2/2010 | Moyers | |
| 2013/0247320 A1 * | 9/2013 | Bayham | ................. A47K 7/028 15/145 |
| 2020/0154954 A1 | 5/2020 | Mesue | |

FOREIGN PATENT DOCUMENTS

WO　　WO2017193941　　11/2017

* cited by examiner

*Primary Examiner* — Shay Karls

(57) ABSTRACT

A compressed body exfoliating device for ameliorating the process of exfoliating the body includes a base. The base is grasped by a hand of the user. The base has a circular shape with a sponge surface and a hand surface. A exfoliating mesh fabric is adhered on the sponge surface of the base. The exfoliating mesh fabric has a spiral shape upon the sponge surface of the base wherein the spiral shape is provides equal coverage of the exfoliating mesh fabric upon the surface of the body. Furthermore, an alternate embodiment of the compressed mesh exfoliating device includes the base lacking a circular shape and having an oval shape. The base of the alternate embodiment has a strap attached to the hand surface of the base. The exfoliating mesh fabric of the alternate embodiment has a layered shape.

10 Claims, 4 Drawing Sheets

COMPRESSED BODY EXFOLIATING DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to body sponge device and more particularly pertains to a new body sponge device for ameliorating the process of exfoliating the body.

(2) Description of Related Art Including Information Disclosed Under 37 CFR 1.97 and 1.98

The prior art relates to body sponge devices. The prior art includes a variety of body sponge devices having a mesh material configured for cleaning the body of the user. Known prior art lacks a body sponge device having a mesh material and a spiral shape configured for providing equal coverage from the exfoliating mesh fabric upon the body wherein ameliorating the process of cleaning the body.

BRIEF SUMMARY OF THE INVENTION

An embodiment of the disclosure meets the needs presented above by generally comprising a base. The base is configured for being grasped by a hand of the user. The base has a circular shape with a sponge surface and a hand surface. A exfoliating mesh fabric is adhered on the sponge surface of the base. The exfoliating mesh fabric is a strip has a first end and a second end. The exfoliating mesh fabric enwinds about itself wherein the second end is positioned within a center of the sponge surface of the base. The exfoliating mesh fabric has a spiral shape upon the sponge surface of the base wherein the spiral shape is configured for providing equal coverage of the exfoliating mesh fabric upon the surface of the body. Furthermore, an alternate embodiment of the compressed mesh exfoliating device includes the base lacking a circular shape and having an oval shape. The base of the alternate embodiment has a strap adhered to the hand surface of the base. The exfoliating mesh fabric of the alternate embodiment is repeatedly folded from the first end to the second end of the exfoliating mesh fabric wherein the exfoliating mesh fabric of the alternate embodiment has a layered shape.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
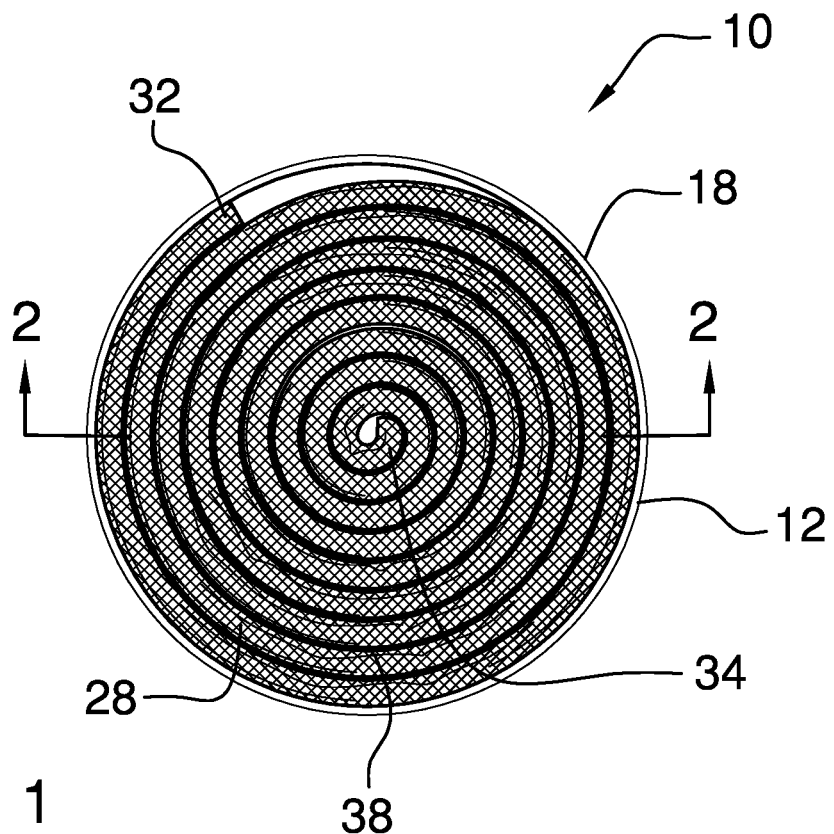
FIG. 1 is a top view of a compressed body exfoliating device according to an embodiment of the disclosure.
Figure 2:
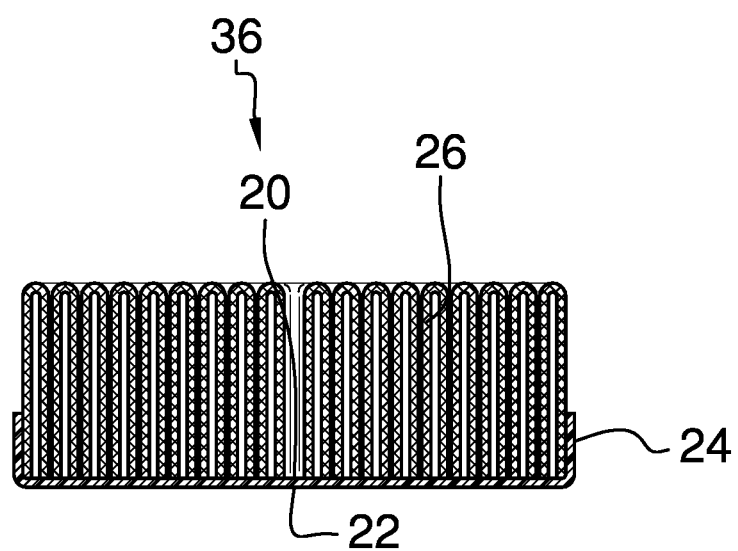
FIG. 2 is a front view of an embodiment of the disclosure.
Figure 3:
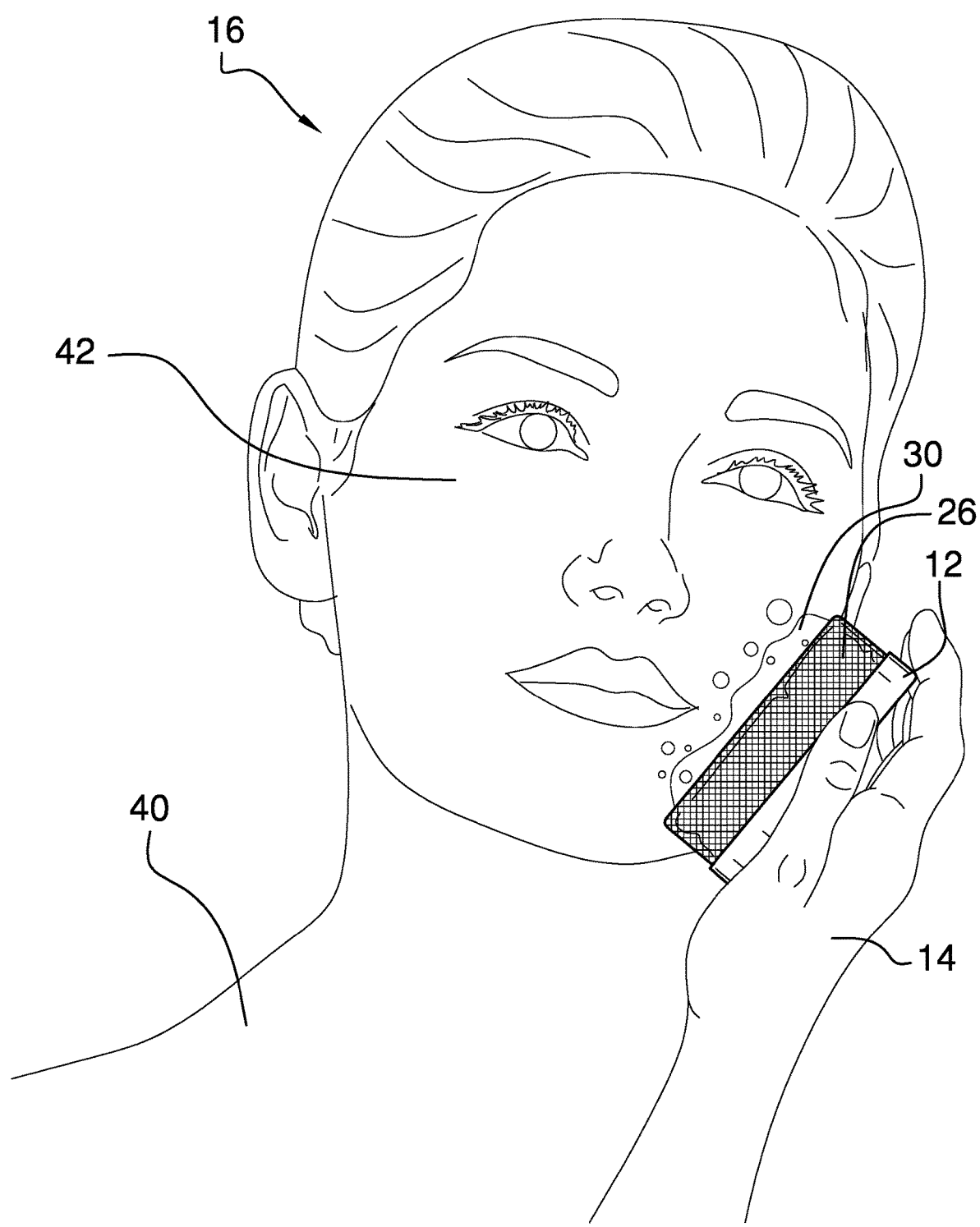
FIG. 3 is an in-use view of an embodiment of the disclosure.
Figure 4:
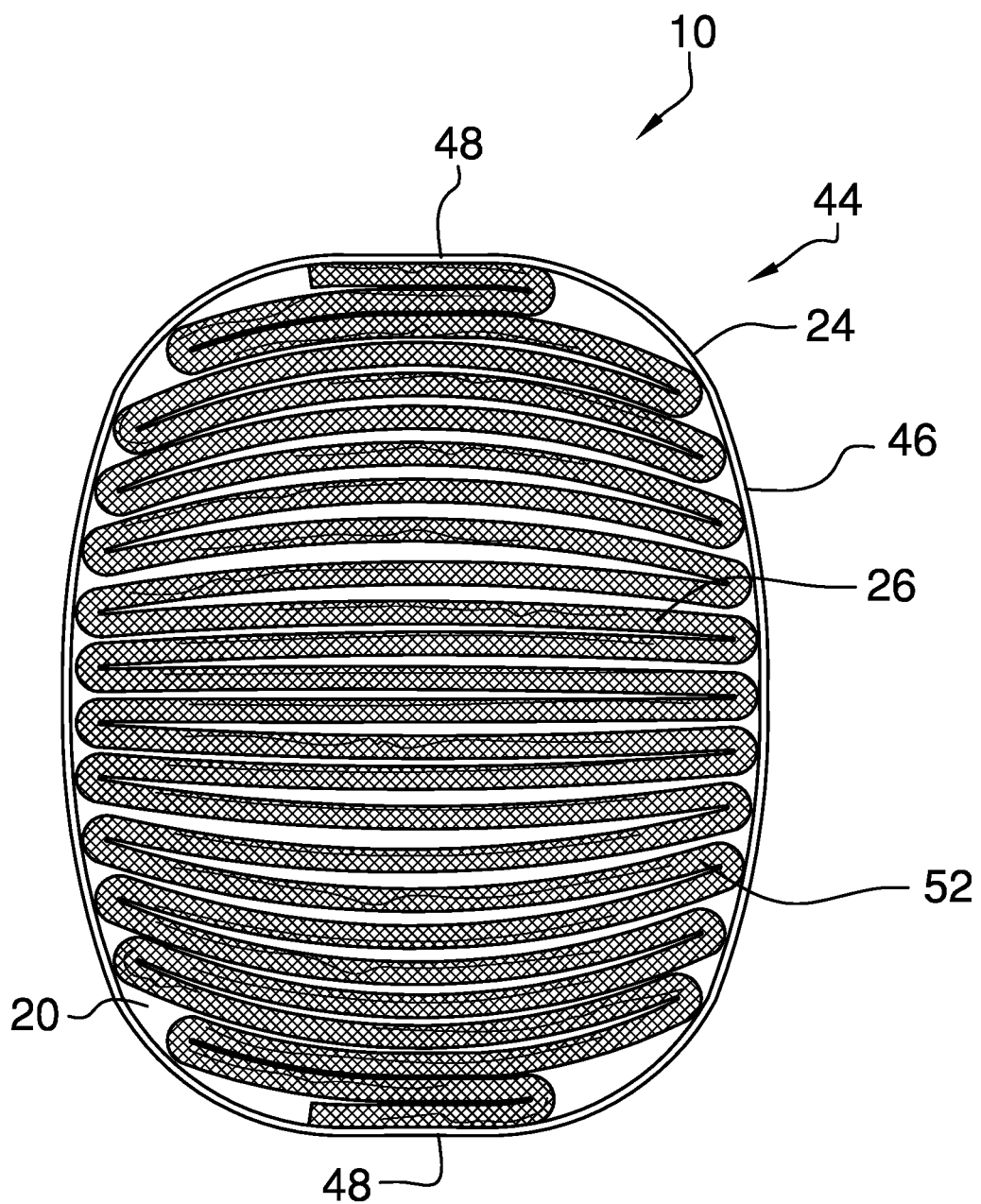
FIG. 4 is a top view of an alternate embodiment of the disclosure.
Figure 5:
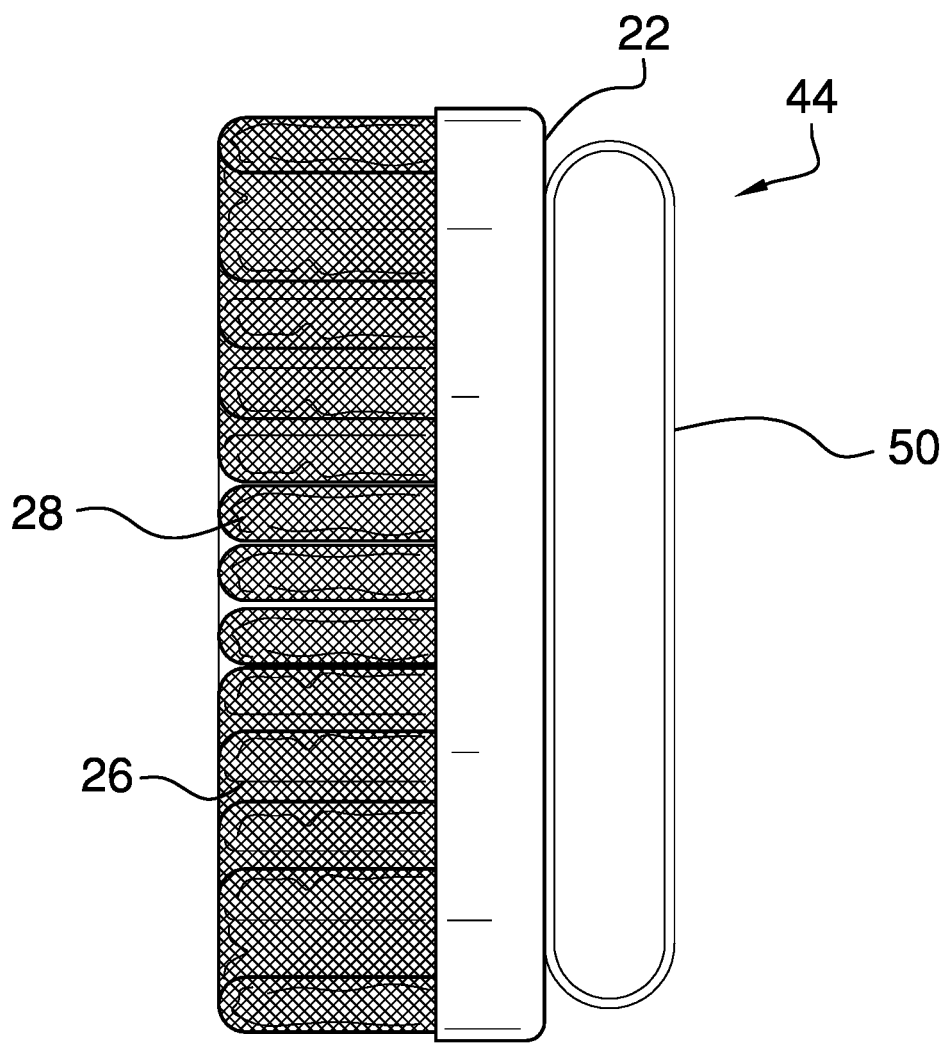
FIG. 5 is a side view of an alternate embodiment of the disclosure.

With reference now to the drawings, and in particular to FIGS. 1 through 5 thereof, a new body sponge device embodying the principles and concepts of an embodiment of the disclosure and generally designated by the reference numeral 10 will be described.

As best illustrated in FIGS. 1 through 5, the compressed body exfoliating device 10 generally comprises a base 12. The base 12 is configured for being grasped by a hand 14 of the user 16. The base 12 has a circular shape 18 having a sponge surface 20 and a hand surface 22. Furthermore, the base 12 has a perimeter wall 24 protruding out from the sponge surface 20. The base 12 is configured to be within a range of sizing to fit within the palm of the hand 14 of the user 16. The base 12 is a waterproof material being configured for being liquid impervious. The waterproof material of the base 12 is meant to reduce damage to the base 12 from constant exposure to water.

A exfoliating mesh fabric 26 is adhered on the sponge surface 20 of the base 12. The exfoliating mesh fabric 26 is a mesh material 28 being configured for being soft relative to the body of the user 16. The exfoliating mesh fabric 26 is configured for retaining a liquid mixture 30 wherein the liquid mixture 30 includes soap and water. The liquid mixture 30 is used to wash the body 40 of the user 16. The exfoliating mesh fabric 26 is a strip has a first end 32 and a second end 34. The first end 32 is positioned adjacent to the perimeter wall 24 of the base 12. The exfoliating mesh fabric 26 enwinds about itself wherein the second end 34 is positioned within a center 36 of the sponge surface 20 of the base 12. The exfoliating mesh fabric 26 has a spiral shape 38 upon the sponge surface 20 of the base 12 wherein the spiral shape 38 is configured for providing equal coverage of the exfoliating mesh fabric 26 upon the surface of the body 40. The equal coverage of the exfoliating mesh fabric 26 upon the surface of the body 40 ameliorates the process of cleaning the body 40. The spiral shape 38 is configured for use upon the face 42 of the user 16.

An alternate embodiment 44 of the compressed mesh exfoliating device 10 includes the base 12 lacking a circular shape 18 and having an oval shape 46. The perimeter wall 24 of the base 12 of the alternate embodiment has a pair of heads 48 being positioned parallel relative to each other. The base 12 of the alternate embodiment 44 has a strap 50 adhered to the hand surface 22 of the base 12. The strap 50 is configured for enwrapping the hand 14 of the user 16 wherein fastening the base 12 to the hand 14 when in-use. The exfoliating mesh fabric 26 of the alternate embodiment 44 has the first end 32 and the second end 34 being positioned adjacent to a respective one of the pair of heads 48 of the perimeter wall 24. The exfoliating mesh fabric 26 of the alternate embodiment 44 is repeatedly folded from the first end 32 to the second end 34 of the exfoliating mesh fabric 26. The layered shape 52 of the exfoliating mesh fabric 26 of the alternate embodiment 44 is configured for use upon the body 40 of the user 16 rather than the face 42 of the user 16.

In use, the user 16 applies the liquid mixture 30 to the exfoliating mesh fabric 26. Subsequently, the exfoliating mesh fabric 26 washes the face 42 of the user 16. The spiral shape 38 of the exfoliating mesh fabric 26 provides equal coverage of the exfoliating mesh fabric 26 against the skin of the user 16 wherein ameliorating the exfoliation process for the skin of the user 16. Furthermore, the user 16 applies the liquid mixture 30 to the exfoliating mesh fabric 26 of the alternate embodiment 44 prior to washing the body 40 of the user 16. The user 16 can secure the base 12 of the alternate embodiment 44 to the hand 14 by inserting the hand 14 within the strap 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A compressed mesh exfoliating device configured for scrubbing a body of a user, the compressed mesh exfoliating device comprising:
    a base being configured for being grasped by a hand of the user said base having a sponge surface and a hand surface positioned opposite each other; and
    an exfoliating mesh fabric being adhered on said sponge surface of said base, said exfoliating mesh fabric being a strip having a first end and a second end, said exfoliating mesh fabric having a first lateral edge and a second lateral edge which extend between said first end and said second end, said first lateral edge being coupled to said sponge surface of said base, said exfoliating mesh fabric being repeatedly folded from said first end to said second end of said exfoliating mesh fabric in an accordion fashion to form a plurality of layers.

2. The compressed mesh exfoliating device of claim 1, wherein said exfoliating mesh fabric is folded along an axis extending between said first end and said second end, said second lateral edge of said exfoliating mesh fabric being coupled to said sponge surface of said base, said exfoliating mesh fabric defining a folded edge positioned distally from said base.

3. The compressed mesh exfoliating device of claim 1, further comprising said base having a perimeter wall protruding out from said sponge surface, said base being configured to be within a range of sizing to fit within the palm of the hand of the user.

4. The compressed mesh exfoliating device of claim 1, further comprising said base being a waterproof material, said waterproof material being configured for being liquid impervious.

5. The compressed mesh exfoliating device of claim 1, further comprising said exfoliating mesh fabric being a mesh material being configured for being soft relative to the body of the user.

6. The compressed mesh exfoliating device of claim 5, further comprising said exfoliating mesh fabric being configured for retaining a liquid mixture, said liquid mixture including soap and water.

7. The compressed mesh exfoliating device of claim 1 further comprising a perimeter wall of said base having a pair of heads positioned opposite each other and extending between said sponge surface and said hand surface.

8. The compressed mesh exfoliating device of claim 7, further comprising said exfoliating mesh fabric having said first end and said second end being positioned adjacent to a respective one of said pair of heads of said perimeter wall.

9. The compressed mesh exfoliating device of claim 1, further comprising a strap adhered to said hand surface of said base, said strap being configured for enwrapping the hand of the user, said strap forming a loop adjacent to said hand surface, said loop having an axis which extends generally parallel to said hand surface.

10. A compressed mesh exfoliating device configured for scrubbing a body of a user, the compressed mesh exfoliating device comprising:
    a base being configured for being grasped by a hand of the user, said base having a sponge surface and a hand surface positioned opposite each other, said base having a perimeter wall protruding out from said sponge surface, said base is configured to be within a range of sizing to fit within the palm of the hand of the user, said base being a waterproof material, said waterproof material being configured for being liquid impervious, said base having an oval shape, said perimeter wall of said base having a pair of heads positioned opposite each other and extending between said sponge surface and said hand surface;

an exfoliating mesh fabric being adhered on said sponge surface of said base, said exfoliating mesh fabric being a mesh material being configured for being soft relative to the body of the user, said exfoliating mesh fabric being configured for retaining a liquid mixture, said liquid mixture including soap and water, said exfoliating mesh fabric being a strip having a first end and a second end, said exfoliating mesh fabric having a first lateral edge and a second lateral edge which extend between said first end and said second end, said first lateral edge being coupled to said sponge surface of said base, said exfoliating mesh fabric being repeatedly folded from said first end to said second end of said exfoliating mesh fabric in an accordion fashion to form a plurality of layers, said exfoliating mesh fabric being folded along an axis extending between said first end and said second end, said second lateral edge of said exfoliating mesh fabric being coupled to said sponge surface of said base, said exfoliating mesh fabric defining a folded edge positioned distally from said base; and a strap adhered to said hand surface of said base, said strap being configured for enwrapping the hand of the user, said strap forming a loop adjacent to said hand surface, said loop having an axis which extends generally parallel to said hand surface.

* * * * *